(12) United States Patent
Park et al.

(10) Patent No.: US 11,666,858 B2
(45) Date of Patent: Jun. 6, 2023

(54) METHOD FOR DETERMINING PROCESS CONDITIONS TO REMOVE VOLATILE ORGANIC COMPOUNDS FROM POLYMER

(71) Applicant: LG Chem, Ltd., Seoul (KR)

(72) Inventors: Je Seob Park, Daejeon (KR); Won Chan Park, Daejon (KR); Jae Hoon Choi, Daejeon (KR)

(73) Assignee: LG Chem, Ltd.

( * ) Notice: Subject to any disclaimer, the term of this patent is extended or adjusted under 35 U.S.C. 154(b) by 877 days.

(21) Appl. No.: 16/605,584

(22) PCT Filed: Apr. 23, 2018

(86) PCT No.: PCT/KR2018/004665
§ 371 (c)(1),
(2) Date: Oct. 16, 2019

(87) PCT Pub. No.: WO2018/199565
PCT Pub. Date: Nov. 1, 2018

(65) Prior Publication Data
US 2020/0129920 A1 Apr. 30, 2020

(30) Foreign Application Priority Data

Apr. 24, 2017 (KR) .......................... 10-2017-0052045
Apr. 20, 2018 (KR) .......................... 10-2018-0045985

(51) Int. Cl.
*B01D 53/30* (2006.01)
*G16C 60/00* (2019.01)
(Continued)

(52) U.S. Cl.
CPC ........... *B01D 53/30* (2013.01); *B01D 53/025* (2013.01); *G01N 13/00* (2013.01);
(Continued)

(58) Field of Classification Search
CPC ................. B01D 53/30; B01D 53/025; B01D 2257/708; G16C 60/00
See application file for complete search history.

(56) References Cited

U.S. PATENT DOCUMENTS 5,993,515 A * 11/1999 Sirkar ....................... C02F 1/44
 210/321.89
7,025,800 B2 * 4/2006 Campbell .......... B01D 39/1623
 356/477
(Continued)

FOREIGN PATENT DOCUMENTS

CN 102092108 A 6/2011
JP 2005279570 A 10/2005
(Continued)

OTHER PUBLICATIONS

Chinese Search Report for Application No. 201880027208.9 dated Jun. 2, 2021, pp. 1-3.
(Continued)

*Primary Examiner* — Long T Tran
(74) *Attorney, Agent, or Firm* — Lerner David LLP

(57) ABSTRACT

The present application relates to a method for determining process conditions to remove volatile organic compounds from a polymer product through blowing. According to the method of the present application, time and energy can be saved.

19 Claims, 5 Drawing Sheets

Sample 1

(not subjected to blowing)

Sample 2

(subjected to blowing)

(51) Int. Cl.
  *B01D 53/02* (2006.01)
  *G01N 30/86* (2006.01)
  *G06F 30/20* (2020.01)
  *G01N 33/00* (2006.01)
  *G01N 13/00* (2006.01)
  *G06F 111/10* (2020.01)
  *G01N 30/02* (2006.01)

(52) U.S. Cl.
  CPC ..... *G01N 30/8675* (2013.01); *G01N 33/0047* (2013.01); *G06F 30/20* (2020.01); *G16C 60/00* (2019.02); *B01D 2257/708* (2013.01); *G01N 2013/003* (2013.01); *G01N 2030/025* (2013.01); *G06F 2111/10* (2020.01)

(56) References Cited

U.S. PATENT DOCUMENTS

| | | | |
|---|---|---|---|
| 8,543,242 B2 | 9/2013 | Odi | |
| 2003/0200796 A1 | 10/2003 | Pawliszyn | |
| 2008/0008625 A1* | 1/2008 | Thomas | G01N 1/2214 422/91 |
| 2008/0052058 A1* | 2/2008 | Odi | C08F 6/003 703/12 |
| 2009/0311540 A1* | 12/2009 | Cohen | B82Y 40/00 427/535 |
| 2011/0160420 A1* | 6/2011 | Chamayou | C08F 6/001 526/348.3 |
| 2011/0201765 A1 | 8/2011 | Odi | |
| 2011/0223091 A1* | 9/2011 | Miller | B01D 53/18 162/29 |
| 2016/0298450 A1 | 10/2016 | McAlary et al. | |

FOREIGN PATENT DOCUMENTS

| | | |
|---|---|---|
| JP | 2009279523 A | 12/2009 |
| JP | 2010029803 A | 2/2010 |
| KR | 101018455 B1 | 3/2011 |
| KR | 20120132419 A | 12/2012 |

OTHER PUBLICATIONS

International Search Report from Application No. PCT/KR2018/004665 dated Jul. 27, 2018, 2 pages.

* cited by examiner

[Figure 1]
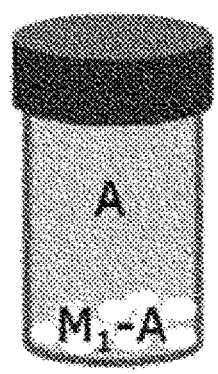 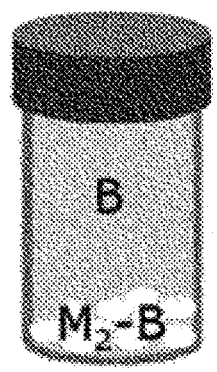
Sample 1                                Sample 2
(not subjected to blowing)      (subjected to blowing)

[Figure 2]
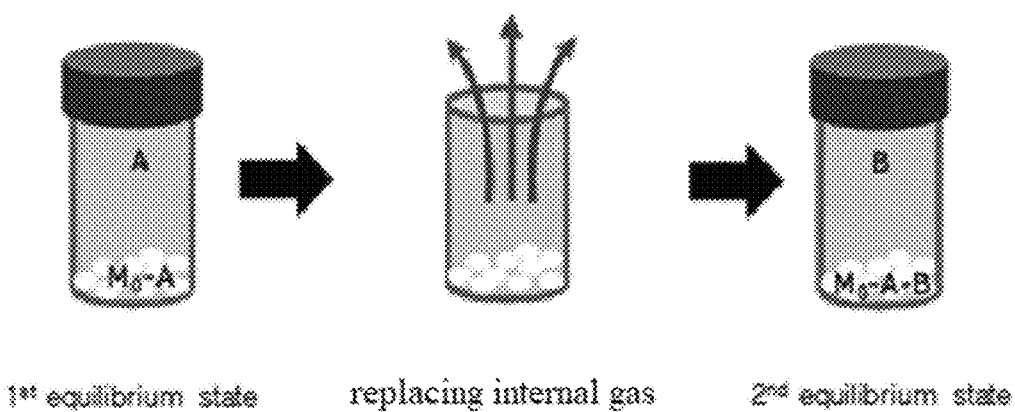

[Figure 3]
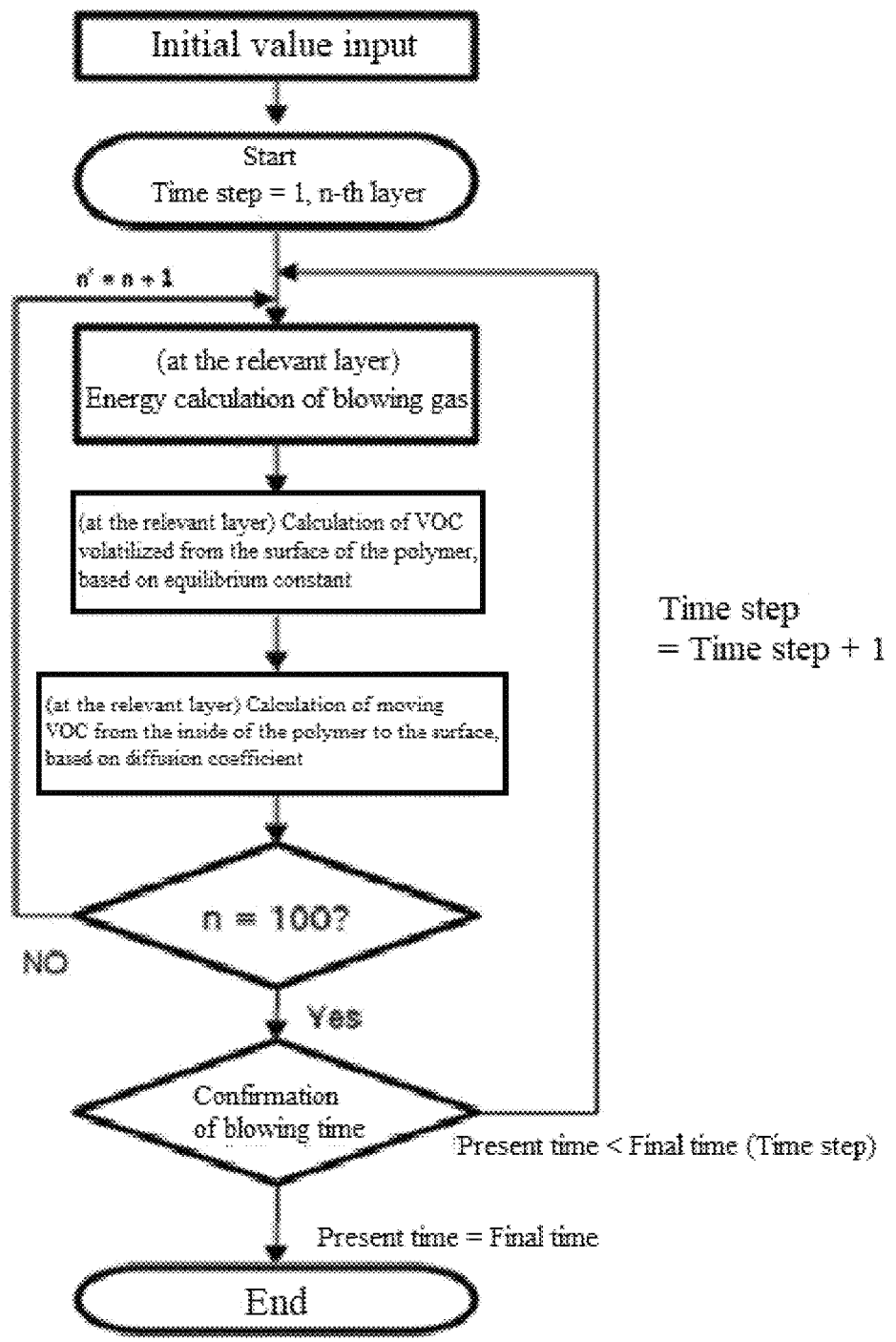

[Figure 4(a)]
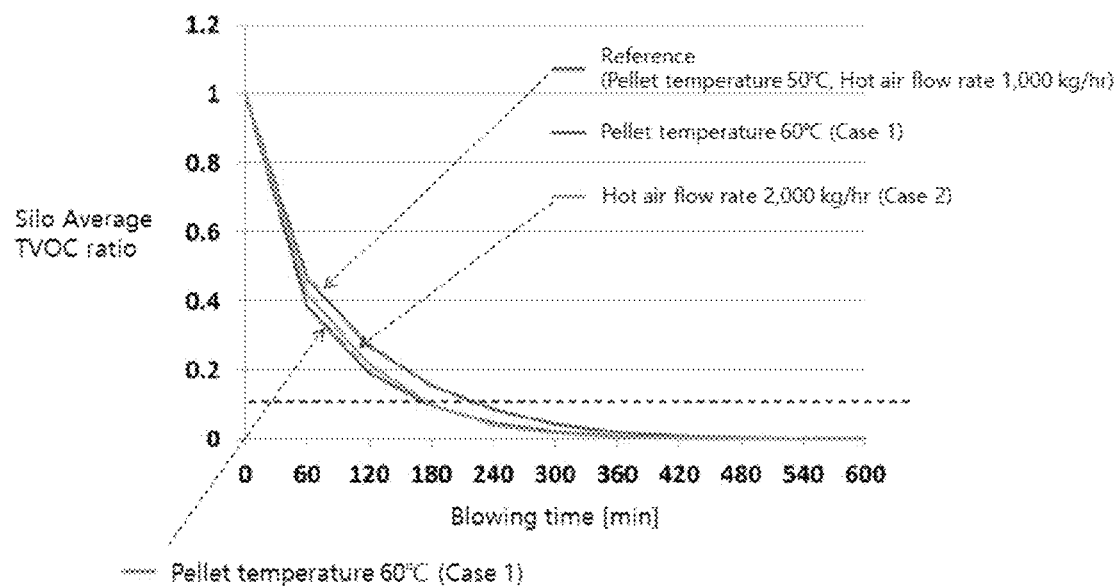
[Figure 4(b)]
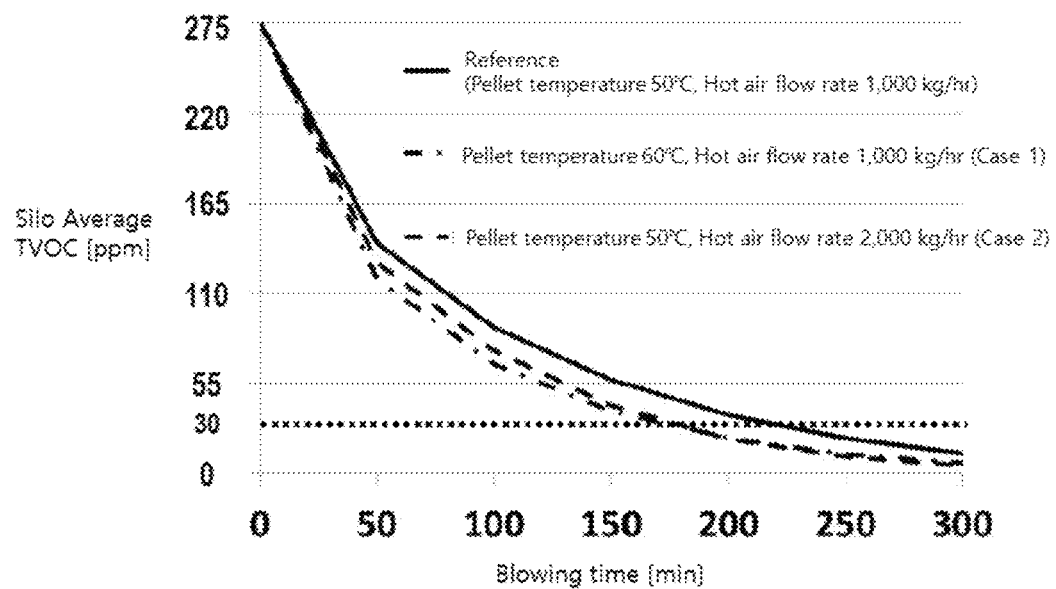

[Figure 5(a)]
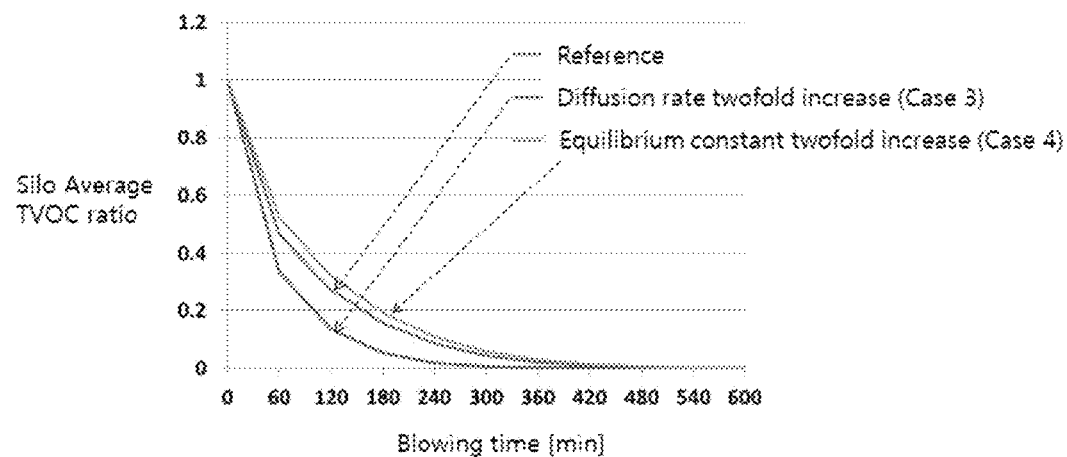
[Figure 5(b)]
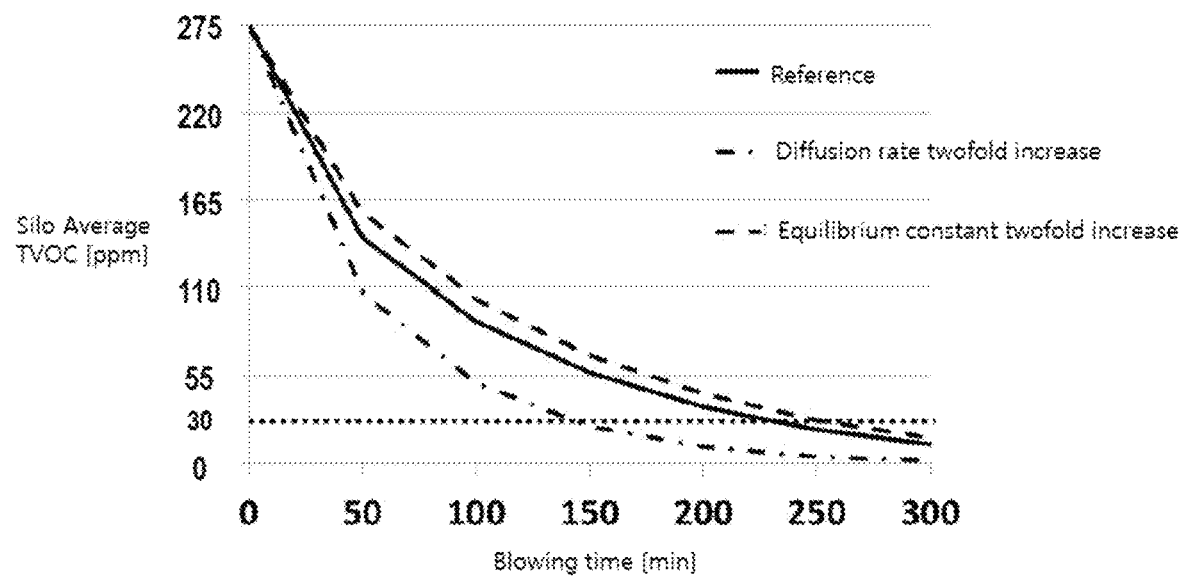

METHOD FOR DETERMINING PROCESS CONDITIONS TO REMOVE VOLATILE ORGANIC COMPOUNDS FROM POLYMER

CROSS-REFERENCE TO RELATED APPLICATIONS

This application is a national phase entry under 35 U.S.C. § 371 of International Application No. PCT/KR2018/004665, filed Apr. 23, 2018, which claims priority based on Korean Patent Application No. 10-2017-0052045, filed on Apr. 24, 2017 and Korean Patent Application No. 10-2018-0045985, filed on Apr. 20, 2018, the disclosures of which are incorporated herein by reference.

TECHNICAL FIELD

The present application relates to a method for determining process conditions to remove volatile organic compounds from a polymer.

BACKGROUND ART

Volatile organic compounds (VOC) are derived from the residues of monomers, solvents, or other components used to make polymer products. Volatile organic compounds remain inside the product or on its surface even after manufacturing the product, and slowly rise over the product surface or are released into the air for a long period of time. These volatile organic compounds may affect the hormone system of the human body through various routes as well as they degrade quality and color senses of the product and cause unpleasant odors.

A post-treatment, that is, removal of volatile organic compounds from the produced polymer product, can be accomplished through, for example, a method of exposing the product in a fresh gas or a method of blowing a fresh gas into the product, and the like. Preferably, it is necessary to remove as much volatile organic compounds as possible and to this end, it should take a long time to expose the product to the gas or blow the gas into the product, but considering realistic factors such as a product delivery time or production deadline, the time required for the post-treatment cannot be indefinitely taken for a long time. In a state where the properties are different for each polymer and each volatile organic compound and the amount of volatile organic compounds and its release rate are also unknown, it is not easy to determine whether the removal process of volatile organic compounds is performed under what conditions and for how much time.

DISCLOSURE

Technical Problem

It is one object of the present application to provide a method for determining process conditions to remove volatile organic compounds from a polymer.

It is another object of the present application to optimize an amount of production, a production deadline and a delivery time of a polymer product, and the like by selecting and regulating a condition for exposing the polymer product to a gas.

The above objects and other objects of the present application can be all resolved by the present application, which is described in detail below.

Technical Solution

In one example of the present application, the method of the present application is a method of determining process conditions to remove volatile organic compounds from a polymer by blowing a gas. The method comprises steps: calculating a diffusion coefficient (D) and an equilibrium constant (K) of a polymer; and simulating a removal process of volatile organic compounds based on the calculated diffusion coefficient and equilibrium constant.

Advantageous Effects

According to the present application, there can be provided a method of capable of analyzing a process of removing volatile organic compounds present in a polymer product from the polymer after simulation, and predicting and determining suitability of the related process.

BRIEF DESCRIPTION OF DRAWINGS

FIG. 1 is shown to assist in understanding an experimental method of calculating a diffusion coefficient (D) according to one example of the present application.

FIG. 2 is shown to assist in understanding an experimental method of calculating an equilibrium constant (K) according to one example of the present application.

FIG. 3 shows a simulation order of a process, according to one example of the present application.

FIG. 4(a) is a graph showing a result of simulating a process of removing volatile organic compounds from a polymer based on diffusion coefficients and equilibrium constants experimentally obtained according to one example of the present application. FIG. 4(b) is a graph showing a result of analysis through the absolute amount of total volatile organic compounds (TVOC).

FIG. 5(a) is a graph showing process results in accordance with change of diffusion coefficients and equilibrium constants experimentally obtained according to one example of the present application. FIG. 5(b) is a graph showing a result of analysis through the absolute amount of total volatile organic compounds (TVOC).

BEST MODE

The present application relates to a method for determining process conditions to remove volatile organic compounds from a polymer product by blowing a gas. The method may comprise steps of: analyzing characteristics of a product; and simulating a process of removing volatile organic compounds.

In the present application, the product or polymer product may be referred to as a "polymer," and the characteristics of a product may be "a diffusion coefficient" and "an equilibrium constant." The diffusion coefficient and the equilibrium constant can be analyzed experimentally. For example, the amount of volatile organic compounds can be measured in a headspace of a container storing a polymer to calculate the diffusion coefficient and equilibrium constant from the measured values. The details are described below.

In the present application, the terms "volatile organic compound" and "polymer" are not limited to a specific compound or polymer but may be used in a meaning embracing compounds that can be referred to as volatile organic compounds in the related technical field, and polymers that can be released from the surface. The amount of volatile organic compounds (VOC) may be referred to as total volatile organic compounds (TVOC).

In the present application, the "blowing" may mean a treatment to cause or blow a flow of oxygen ($O_2$) or nitrogen ($N_2$) or a gas containing it toward the polymer. The temperature of the gas to be blown can be adjusted appropriately, and the flow of a gas for blowing can be suitably caused by those skilled in the art using known methods or equipment.

According to one example of the present application, a method for determining process conditions to remove volatile organic compounds from a polymer by blowing a gas comprises calculating a diffusion coefficient (D) and an equilibrium constant (K) of the polymer; and simulating a process of removing the volatile organic compounds based on the calculated diffusion coefficient and equilibrium constant. In another embodiment, the method may comprise steps of: measuring an amount of volatile organic compounds in a headspace of a container storing a polymer to calculate a diffusion coefficient and an equilibrium constant from the measured value; and simulating a removal process of the volatile organic compounds based on the calculated diffusion coefficient and equilibrium constant. The fact that is based on the diffusion coefficient and the equilibrium constant means that the diffusion coefficient and the equilibrium constant are used as an initial value of the simulation, as described below.

Regarding the calculation of the diffusion coefficient and the equilibrium constant based on the amount of the volatile organic compounds measured in the headspace of the container, the kind of the container storing the polymer is not particularly limited. For example, a container including a body having a predetermined volume and a cap capable of blocking physical movement of a material between the inside and outside of the body, such as a known vial, can be used. That is, it is sufficient that the container usable in the present application can be opened and closed, and if necessary, the inside of the container can be sealed with an external environment. The measurement of the amount of volatile organic compounds is performed on the premise that the system defined by the sealed container containing the polymer is in an equilibrium state.

The determination of the equilibrium state can be made by measuring the change of the total volatile organic compounds plural times over time. For example, if the amount of the volatile organic compounds is measured several times from 30 minutes to 5 hours while storing the polymer at a predetermined temperature such as 120° C., the measured amounts of the volatile organic compounds will converge to a constant value as the storing time increases. That is, it can be determined that the equilibrium state has been reached after the amount of the organic compounds has become constant.

In the present application, the polymer may be stored in a solid form in a container. For example, a polymer or a polymer product can be stored in the form of powders or pellets (e.g., spheres or ellipses) in the container. At this time, the polymer may be stored in the container in a volume smaller than the volume of the container. The container can secure an internal space, that is, a headspace, which is not occupied by the polymer product. Accordingly, volatile organic compounds volatilized from the polymer and a predetermined gas (e.g., air) can occupy the headspace of the container.

In the present application, the method of measuring an amount of the volatile organic compounds present in the headspace of the container is not particularly limited. For example, the amount of the volatile organic compounds present in the headspace can be measured using gas chromatography. The unit representing the amount of the volatile organic compounds is not particularly limited.

With reference to the accompanying drawings, a method of calculating the diffusion coefficient and the equilibrium constant from the measured amount of the volatile organic compounds will be described as follows.

FIG. 1 is shown to assist in understanding an experimental method of calculating a diffusion coefficient (D) of volatile organic compounds included in a polymer. In FIG. 1, two vials are shown, in which pellet-shaped polymers prepared by the same method from the same components are sealed and stored in the same amount, respectively. However, the pellets stored in the right vial were subjected to a blowing treatment and the pellets stored in the left vial were subjected to no blowing treatment. The timing of the blowing treatment for the pellets stored in the right vial is not particularly limited. For example, after the polymer is stored in the container, the blowing can be performed, or before the polymer is stored in the container, the blowing can also be performed.

Specifically, in FIG. 1, $M_1$ is the total amount of volatile organic compounds that the polymer stored in the left vial (Sample 1) has, $M_2$ means the total amount of the volatile organic compounds that the polymer stored in the right vial (Sample 2) has after being subjected to the blowing treatment. On the other hand, when the amount of the volatile organic compounds volatilized from the polymer stored in the left vial after storing the polymer in the vial for a predetermined time, that is, the amount of the gas-phase volatile organic compound present in the headspace of the vial in Sample 1, is A, the amount of the remaining volatile organic compounds that the solid polymer stored in the left vial has (in the inside and/or on the surface) may be defined as $M_1-A$. Here, the predetermined time for which the polymer is stored for measuring the content A may mean a time equal to or longer than the minimum time that can be considered to have reached the equilibrium state as described above. Similarly, when the amount of the volatile organic compounds present in the headspace of the right vial is B after storing the polymer in the right vial for a predetermined period of time, the amount of the remaining volatile organic compounds that the solid polymer of the right vial have (in the inside and/or on the surface) may be defined as $M_2-B$.

In one example, the contents A and B can be measured on the premise that the two samples have reached the equilibrium state at the same temperature (t).

When they reach the equilibrium state at the same temperature condition, the equilibrium constant (K) values obtained from the respective vials shown in FIG. 1 are the same. Then, the equilibrium constant (K) can be obtained through a ratio between 'the amount of volatile organic compounds that air in a unit volume has in the headspace' and 'the amount of volatile organic compounds that the polymer in a unit volume has.' The polymer may have a particle shape such as pellets. Accordingly, the following relation equation 1 is established.

$$K = \frac{C_{s1}}{C_{g1}} = \frac{C_{s2}}{C_{g2}} \qquad \text{[Equation 1]}$$

⟨-⟩

$$\frac{M_1 - A}{V_s} \bigg/ \frac{A}{V_g} = \frac{M_2 - B}{V_s} \bigg/ \frac{B}{V_g} \qquad \text{[Equation 2]}$$

Therefore, the following relation equation 1 is obtained.

$$M_2 = \frac{B}{A} \cdot M_1 \qquad \text{[Relation Equation 1]}$$

In Equations above, $C_{g1}$ is the amount of volatile organic compounds that air in a unit volume has in the headspace in Sample 1, and $C_{s1}$ means the amount of volatile organic compounds that the polymer in a unit volume has in Sample 1. In addition, $C_{g2}$ is the amount of volatile organic compounds that air in a unit volume has in the headspace in Sample 2, and $C_{s2}$ means the amount of volatile organic compounds that the polymer in a unit volume has in Sample 2. Then, in each of Samples 1 and 2, $V_s$ is the volume of the entire polymer in the vial, and $V_g$ is the volume of the headspace, i.e., the volume of air present in the headspace. In one example, $V_s$ can be obtained from the density and weight of the selected pellets, and $V_g$ can be obtained from the value of the internal volume of the used container (vial) minus $V_s$.

From Equations 1 and 2 and Relation Equation 1 concerning the equilibrium constants as described above, it can be seen that the ratio (B/A) value of the volatile organic compounds measured in Samples 1 and 2, respectively is the same as $M_2/M_1$.

On the other hand, when volatile organic compounds are released from spherical particles, the diffusion coefficient (D) can be obtained by the following formula. Details of the formula can be found in Chapter Diffusion in a sphere of The Mathematics of Diffusion (2nd Edition), which is J. Crank's book.

$$\frac{M_t}{M_\infty} = 1 - \frac{6}{\pi^2} \sum_{n=1}^{\infty} \frac{1}{n^2} \exp(-Dn^2\pi^2 t/a^2) \qquad \text{[Formula]}$$

The formula is that the formula in the integral form associated with the calculation of the diffusion coefficient is changed to the form of infinite series. Therefore, it may be correct to use the formula after summing up the calculated values from the case where the value of n is 1 to the case where it is infinite, but since there is $n^2$ in the denominator, when n is an integer exceeding about 10, the effect of the n value is not significant. In other words, in the formula, it is also fine to perform the calculation only when n is from 1 to 10.

In the formula, $M_\infty$ is the total amount of volatile organic compounds that the particles can discharge for the infinite time (i.e., while reaching the equilibrium sate without blowing), and $M_t$ is the total amount of volatile organic compounds that the particles have after the particles discharge the volatile organic compounds for a certain time through blowing. Thus, $M_\infty$ may correspond to $M_1$ as described above, and $M_t$ may correspond to $M_2$ as described above. As a result, it can be said that the value of B/A measured in the headspace is equal to the value of $M_t/M_\infty$. And, in the formula, t may be the blowing time (an example of unit: hour), and a may be the particle size of the polymer (an example of unit: mm). Consequently, when these values are substituted into the formula, the D value described in the formula, that is, the diffusion coefficient can be obtained.

FIG. 2 is shown to assist in understanding the calculation of the equilibrium constant (K) of the volatile organic compounds contained in the polymer. As shown in FIG. 2, after one sample sequentially reaches two equilibrium states, the equilibrium constant (K) can be obtained through the amount of volatile organic compounds in the headspace measured in each equilibrium state.

Specifically, as shown in FIG. 2, a polymer containing volatile organic compounds as much as $M_0$ (for example, a polymer having a particle shape such as pellets) is sealed and stored in one container (e.g., vial), and stored for a predetermined time so as to be capable of reaching a first equilibrium state. When the amount of the volatile organic compounds present in the headspace after a lapse of a predetermined time is A, the amount of the volatile organic compounds remaining in the polymer may be defined as $M_0$–A. Then, the inner gas of the sample is replaced through a method of opening the cap of the vial, or the like, and the cap is closed again. The opening time is not particularly limited. After a lapse of a predetermined time, it reaches a second equilibrium state, and then when the amount of the volatile organic compounds present in the headspace is B, the amount of volatile organic compounds remaining in the polymer may be defined as $M_0$–A–B. At this time, the first and second equilibrium states may be formed at the same temperature (t').

When the equilibrium states are reached at the same temperature condition, the values of the equilibrium constant (K) obtained in the first and second equilibrium states shown in FIG. 2 are the same. Then, the equilibrium constant (K) can be obtained through a ratio between 'the amount of volatile organic compounds that air in a unit volume has in the headspace' and 'the amount of volatile organic compounds that the polymer in a unit volume has.' In the following equations 3 and 4, however, $V_s$ is the volume of the entire polymer in the vial and $V_g$ is the volume of the headspace, i.e., the volume of air present in the headspace, where these values are values already known at the time of vial selection and introduction of the polymer.

$$K = \frac{M_1 - A}{V_s} \bigg/ \frac{A}{V_g} = \frac{M_2 - A - B}{V_s} \bigg/ \frac{B}{V_g} \qquad \text{[Equation 3]}$$

⟨-⟩

$$M_0 = \frac{A^2}{A - B} \qquad \text{[Equation 4]}$$

If the result of Equation 4 above is substituted into Equation 3, the following relation equation 2 can be obtained.

$$K = \left(\frac{B}{A - B}\right) \cdot \frac{V_g}{V_s} \qquad \text{[Relation Equation 2]}$$

Consequently, A and B can be measured through gas chromatography, and since the values of $V_s$ and $V_g$ are already known values, the equilibrium constant (K) can be obtained through Relation Equation 2 above.

In one example, the equilibrium state temperatures used to obtain the equilibrium constant (K) and the diffusion coefficient (D), respectively, may be the same or different. For example, both the equilibrium constant and the diffusion coefficient can be calculated at 60° C. Alternatively, the equilibrium constant and the diffusion coefficient may be analyzed at 40° C., 60° C. and 80° C., and then the diffusion coefficient and the equilibrium constant at 50° C. may be deduced and used in the method of the present application. For example, K values obtained at three temperatures (T) of 40° C., 60° C. and 80° C. are used to be substituted into $K=10^{((b/T)-C)}$, whereby b and C can be obtained and then the K value at a specific temperature T can be obtained. The used formula can be found in B. Kolb & L. Ettre' book, 'Static Headspace-Gas Chromatography.'

In another example, the values of the equilibrium constants and/or the diffusion coefficients may be calculated at a plurality of temperatures. For example, the values of the equilibrium constant and the diffusion coefficient at each temperature can be calculated at 0.1° C. intervals, 0.5° C. intervals, 1° C. intervals, 2° C. intervals or 3° C. intervals in a temperature range of 20° C. to 100° C. The values calculated at a plurality of temperatures can be appropriately used at a stage where the corresponding value is required in a simulation process to be described below.

According to the method of the present application, it is possible to simulate a process of removing volatile organic compounds from a polymer based on the diffusion coefficient and the equilibrium constant calculated in the above manner. Assuming that the polymer is subjected to blowing in a state where the diffusion coefficient and the equilibrium constant, and the like are known, the simulation is that the results are confirmed. After confirming the results, suitability of process conditions, and the like can be interpreted. For example, in the case of simulating a blowing process performed under a predetermined condition, it is possible to check how the TVOC changes with time as in FIG. 4, where the suitability of process conditions is interpreted through the confirmed results.

Specifically, the blowing process to be simulated is assumed to be a process of blowing a gas having a predetermined temperature into a silo loading and storing the polymer at a predetermined height. Then, the simulation is performed while energy balance, material balance and/or their changes in the silo are calculated. In one example of this simulation process, the polymer loaded and stored in the silo may be in the form of particles, such as, for example, pellets. In another example of the simulation process, the gas to be blown has a temperature higher than the polymer, which may be referred to as hot air. Furthermore, the silo may have a cylinder or column shape, and may be assumed to be unaffected other than the matters considered in the present application.

A predetermined program may be used for this simulation. For example, the calculation involved in each step of the simulation may be performed by instructions being executable by a processor and stored on a computer-readable medium. Then, the results of the simulation can be viewed by a performer of the method according to the present application through a display device interlocked with the program performing each step.

In one example, the silo and the polymer can be assumed to be divided into n in the loading height direction. For example, in the case where the loading height of the polymer in the silo is 10 m, it can be assumed that if the loaded polymer is evenly divided into 100, one unit of the polymer loaded at a height of 10 cm is present in each of layers equally divided into 100 (may be referred to as unit or unit cell). That is, it can be assumed that the silo is equally divided into n layers including a polymer having the same loading height. Then, it can be assumed that each of the divided silos secures an extra space (e.g., headspace) in which the volatile organic compounds released from the polymer can exist. Then, the energy balance and the material balance can be sequentially calculated for each of the layers. For example, the energy balance and the material balance can be sequentially calculated from the first layer to the n-th layer by a method that the energy balance and the mass balance are calculated while the blown gas passes through the first layer and the same calculation is performed even if the gas passing through the first layer continuously passes through the second layer. At this time, the energy balance and the material balance calculated in association with the n−1-th layer can be used for the energy balance and the material balance calculation of the n-th layer.

A specific simulation process will be described with reference to FIG. 3.

As in FIG. 3, the simulation may comprise a step of inputting an initial value including a diffusion coefficient and an equilibrium constant. That is, the simulation of the blowing process is performed based on predetermined information related to process conditions. Specifically, in order to simulate the blowing process, some information related to the process may be inputted as an initial value into the program used to perform the method of the present application. As the initial value, the experimentally calculated diffusion coefficient and equilibrium constant can be used.

In one example, other information besides the diffusion coefficient and equilibrium constant may be used together as an initial value. For example, one or more selected from the group consisting of a size of a polymer (e.g.: diameter of a particle type polymer), characteristics of a polymer (e.g.: mass, specific heat and/or density), a temperature of a blowing gas, a flow rate of a blowing gas, specific heat of a blowing gas, a blowing time of a gas, a loading height of a polymer in a silo, bulk density of a polymer loaded in a silo, a temperature of a polymer, the number of layers in the divided silo, TVOC contained in a polymer, and a size of a silo (e.g.: diameter) may be used as additional initial values.

In FIG. 3, the time step means a time during which in the case where the polymer is divided into n layers, interpretation (calculation of material balance and energy balance) from the first to the n-th layers is performed only once without repetition. For example, assuming that the number of repetitions of interpretation from the first to the n-th layers is 100 and the total interpretation time is 100 seconds, the time step means 1 second. In other words, if the interpretation according to the one time step performed for one second is repeated 100 times, the time required for the total time steps, that is, the total interpretation time is 100 seconds. In the present application, the interpretation as above is made during the time that the gas is blown. In other words, the total time for which the interpretation as above is performed means the total time for which the blowing is performed, and the time step, which is a time for which the above-described one time analysis is performed, is a concept defined for the simulation, which can mean the unit time when a fresh gas (divided from the first layer to n-th layer) is blown into a silo. Consequently, in the present application, the total interpretation time, i.e., the total blowing time, can be divided into a plurality of time steps. In some cases, the gas may be seen to flow continuously or discontinuously into the silo during one unit of time step.

Furthermore, in the present application, it can be assumed that a fresh gas is periodically blown into the first layer of the silo when the order of the time steps is changed. For example, if the analysis during the first time step performed assuming that the fresh gas continuously passes through from the first layer to the n-th layer is completed, the second analysis, that is, the second time step, in which the fresh gas again passes through from the first layer to the n-th layer, begins.

With respect to the analysis, the n-th calculated value can affect the calculated value of the n+1-th layer, and the calculated value at the m-th time step can affect the calculated value at the m+1-th time step. It will be explained in more detail in the related contents.

Considering accuracy of the interpretation, the shorter the physical time of one time step, the better. Even if the total time required for the interpretation is the same, the shorter the physical time of one time step, the number of interpretation from the first to the n-th layers can increase and the accuracy can increase. For example, it is preferred that one time step is set to mean a time of several seconds to tens of seconds. Also, the interval between time steps is also preferably as short as possible.

Specifically, the simulation may comprise: a first step of using an energy balance calculation between a polymer and a blowing gas present in the n-th layer to calculate a changed temperature of the polymer and a changed temperature of the blowing gas; a second step of calculating an amount of volatile organic compounds discharged from the polymer present in the n-th layer; and a third step of calculating an amount of the volatile organic compounds moving from the inside of the polymer present in the n-th layer to the surface of the polymer.

In one example, the first step may be a step of using an energy balance calculation between the polymer and the blowing gas of the n-th layer to calculate 'the elevated temperature of the polymer increased by the gas blown at the n-th layer' and 'the temperature of the gas (hot air) decreased after blowing at the n-th layer.'

Specifically, in order to allow the volatile organic compounds on the surface of the polymer to be discharged into the air, the gas to be blown may have a temperature higher than the temperature of the polymer or the temperature of the air occupying an empty space in the silo assuming that the polymer is stored (for convenience of explanation only, the temperature of the gas flowing into the unit layer is not always higher than the temperature of the polymer present in the relevant layer). When the high-temperature gas or the hot air is blown as above, the thermal energy of the high-temperature gas is transferred to the polymer, and thus the temperature of the polymer consequently increases as compared with that before blowing, and the temperature of the blown gas decreases. The energy balance between the polymer (particle) and the gas to be blown can be expressed as Equation 5 below.

$$Q = H \times A \times (T_A - T_s) \quad \text{[Equation 5]}$$

In Equation 5 above, Q is the energy supplied to the polymer by the gas to be blown, which may have a unit such as W or J. Then, H is a convection heat transfer coefficient, A is an area of particles, $T_A$ is a temperature of the blowing gas, and $T_s$ is a surface temperature of the polymer. The thermal conductivity H of a polymer can be known from known material information or a known relationship, and Ts or $T_A$ is one of the initial input values as described above.

When the thermal energy Q transmitted to the polymer (particle) by the hot air is obtained through Equation 5 above, 'the temperature of the polymer raised by the hot air' and 'the temperature of the hot air dropped after the thermal energy is transmitted to the polymer' can be calculated, respectively. For example, when the Q value is divided by the mass and the specific heat value of the polymer, respectively, the temperature change amount ($\Delta T$) of the polymer can be known, and when the temperature change amount is added to the Ts value, the final temperature of the polymer increased by hot air can be known. Similarly, when the Q value is divided by the mass and the specific heat value of the air, respectively, the temperature change amount ($\Delta T'$) of the air can be known, and when the temperature change amount is added to the $T_A$ value, the final temperature of the air decreased while being blown can be known.

The 'temperature of the blowing gas dropped in the n-th layer' thus obtained can be used as the temperature of the gas flowing (blowing) into the n+1-th layer at the same time step. Then, 'the elevated temperature of the polymer in the n-th layer' thus obtained can be used as the temperature of the polymer present in the n-th layer in the next time step.

In one example, the second step may be a step of calculating an amount (X) of volatile organic compounds discharged from the polymer in the n-th layer. At this time, the equilibrium constant (K) calculated through experimental measurement may be used.

The amount (X) of volatile organic compounds can be regarded as an amount of the compounds present on the surface of the polymer, which are the volatile organic compounds volatilized from the polymer through blowing. In other words, the amount (X) of the discharged volatile organic compounds is the amount of the volatile organic compounds contained in the blowing gas introduced into the n-th layer. That is, it is the amount of volatile organic compounds in the hot air present in the n-th layer.

To calculate the amount (X) of the volatile organic compounds in the hot air, the previously calculated equilibrium constant (K) may be used. That is, when the hot air is blown, the amount of the volatile organic compounds volatilized from the surface of the polymer to be included in the hot air is determined by the equilibrium constant. The equilibrium constant (K) may be expressed as a ratio of 'the amount (VOCs) of the volatile organic compounds present on the surface of the polymer (particle) in the unit volume' to 'the amount (X) of the volatile organic compounds in the unit volume of air.' That is, an equilibrium constant (K)= $(VOCs/V_s)/(X/V_A)$. Consequently, the amount (X) of the volatile organic compounds can be obtained as in Equation 6 below.

$$\text{Amount (X) of volatile organic compounds} = \{(VOCs/V_s)/(K)\} \times V_A \quad \text{[Equation 6]}$$

In Equation 6 above, VOCs is an amount of volatile organic compounds present on the surface of the polymer, $V_s$ is a volume of the polymer surface layer, $V_A$ is a volume of the gas to be blown, and K is an equilibrium constant.

With regard to Equation 6 above, it can be assumed that the polymer is formed by layering a plurality of spheres having different diameters, where $V_s$ means a (inner) volume that the surface of the outermost sphere has. In some cases, it is necessary to check the number of particles when calculating the VOCs. The number of particles can be known from the already known diameter of the silo, the particle loading height, and the bulk density at which the particles are loaded.

With regard to Equation 6 above, the VOCs may be a value measured for a sample that has not been subjected to blowing in the calculation procedure of the experimental diffusion coefficient (D) as described above. Then, K is the initial value known from the experimental calculation, $V_A$ is one of the initial values as the flow rate of the hot air, that is, the gas to be blown, and $V_s$ is the size of the polymer, which is a value that can be known as one of the initial values. In one example, the K value may be one or more of the K values at various temperatures as previously obtained experimentally, where the temperature may be a temperature of the gas blown to the layer.

As described above, as the volatile organic compounds have moved from the surface of the polymer to the air, the amount of the volatile organic compounds contained in the gas blown to the n+1-th layer increases, and on the basis of this, the discharge amount of the volatile organic compounds at the n+1-th layer is calculated. Specifically, the amount (X) of the volatile organic compounds contained in the gas blown in the n-th hot air can be used as the amount of the volatile organic compounds contained in the gas flowing into the n+1-th layer. In one example, when a gas having volatile organic compounds in an amount of X is blown to the n+1-th layer, it can be confirmed using an equilibrium constant (K) whether the volatile organic compounds are further discharged (or volatilized) from the polymer having a predetermined amount of volatile organic compounds on the surface (present at the n+1-th). Specifically, when the value of the equilibrium constant $K_{N+1}$ obtained through 'the amount of volatile organic compounds that the polymer in a unit volume contained in the n+1-th layer has' and 'the amount (X) of volatile organic compounds that the gas in a unit volume blown into the n+1-th layer has' is smaller than the value of the experimentally obtained equilibrium constant K, it can be seen that the additional discharge of the polymer can also occur at the n+1-th layer.

In one example, it can be assumed that the amount (X) of volatile organic compounds has little effect on the next ranked time step.

In one example, the third step may be a step of calculating an amount (Y) of volatile organic compounds moving from the inside of the polymer present in the n-th layer to the surface of the polymer. As previously described, when the volatile organic compounds are volatilized from the surface of the polymer to air, a concentration gradient of the volatile organic compounds occurs between the inside and the surface of the polymer, and thus the volatile organic compounds inside the polymer move to the surface of the polymer. Then, the amount of volatile organic compounds moving from the inside of the polymer to the surface of the polymer can be calculated based on the diffusion coefficient (D). For example, the amount (Y) of the volatile organic compounds moving from the inside of the polymer to the surface of the polymer can be calculated by Equation 7 below, which is a diffusion control equation in a spherical polymer (particle).

$$\frac{\partial C}{\partial t} = \frac{1}{r^2}\frac{\partial}{\partial r}\left\{r^2 D \frac{\partial C}{\partial r}\right\}$$ [Equation 7]

In Equation 7 above, t is a time, D is a diffusion coefficient, r is a radius of the polymer (particle), and C is a concentration. In one example, the D value may be one or more of the D values at various temperatures as previously obtained experimentally, where the temperature may be a temperature of the gas blown to the relevant layer. The amount (Y) of volatile organic compounds on the surface of the polymer moving from the inside of the polymer to the surface of the polymer during the blowing time can be obtained by calculating the change in the concentration with time.

The amount (Y) of volatile organic compounds thus obtained on the surface of the polymer can be used as the amount (VOCs) of volatile organic compounds on the surface of the polymer used in association with Equation 6 at the next time step.

In one example, it can be assumed that the amount (Y) of volatile organic compounds on the surface of the polymer has little effect on the n+1-th layer.

Consequently, in the case of performing the first to third steps as above, that is, as a result of the simulation, (a) the temperature of the polymer, (b) the amount (TVOC) of volatile organic compounds present in the inside and/or on the surface of the polymer, (c) the temperature of the gas blown or to be blown, and (d) the amount (TVOC) of volatile organic compounds contained in the gas blown or to be blown can be known. Among these, (b) the amount (TVOC) of volatile organic compounds present in the inside and/or on the surface of the polymer can be directly used (calculated) for the analysis of the simulation results.

In one example, the simulation results can be analyzed through an average $(Y_{avg})$ of the amount of volatile organic compounds on the surface of the polymer present in each layer after the total interpretation time is over. For example, by obtaining an arithmetic average value $(Y_{avg})$ for the amount of volatile organic compounds measured in the layer for each time step and confirming the decreasing trend of the value $(Y_{avg})$ over time, that is, according to the increase of the time step, the reduction degree of the volatile organic compounds according to the blowing conditions can be compared (see FIG. 4).

In one example, the method may further comprise a step of evaluating suitability or validity of process conditions based on the simulation results and reflecting it in the process conditions. For example, if the result according to the input initial value is appropriate as the current situation, the conditions input as the initial value can be determined as conditions of the actual blowing process, and otherwise, other conditions can be input to perform the simulation again.

With reference to FIGS. 4 and 5, the process of performing the method of the present application will be described in detail as follows.

FIG. 4 shows a result of simulating a process of removing volatile organic compounds from a polymer based on empirically obtained diffusion coefficients and equilibrium constants, as described above. The process of obtaining diffusion coefficients and equilibrium constants on which the simulation is based, and the analysis of the simulation results are as follows.

Calculation of Equilibrium Constants

As previously described with reference to FIG. 2, for one vial sample storing a pellet-shaped polymer in a predetermined volume, the gas inside the vial was changed once between first and second equilibrium states so that two equilibrium states could be obtained sequentially. The amount of volatile organic compounds in the headspace measured at each equilibrium state was measured by gas chromatography at 60° C. Since the weight of the used pellets was 2 g and the density of the polymer constituting the pellets was 1,070 kg/m³, the volume $V_s$ (about 1.87 ml) of the pellets could be obtained from them. On the other hand, as the volume of the headspace, that is, the volume $V_g$ of gas (air), the value obtained by subtracting $V_s$ (about 1.87 ml) from the volume 20 ml of the used vial was used.

In this regard, the TVOC values measured in the first and second equilibrium states and the equilibrium constant (K) obtained according to Relation Equation 2 are as shown in Table 1 below. The known VDA277 method was used upon measuring the amount (TVOC) of volatile organic compounds.

TABLE 1

| | TVOC (ppm) | Equilibrium Constant (K) |
|---|---|---|
| First equilibrium state (at 60° C.) | 157.2 | 124.1 |
| Second equilibrium state (at 60° C.) | 145.8 | |

Calculation of Diffusion Coefficients

As previously described with reference to FIG. 1, two groups of pellet-shaped polymers (particle size: 3 mm), which differed only in the presence or absence of the blowing treatment, were stored in two vials different from each other, respectively, and the amount of volatile organic compounds in the headspace measured at each equilibrium state was measured by gas chromatography at 60° C. The blowing treatment associated with Sample 2 was done for 2 hours. The size of the vial and the volume and weight of the polymer are the same as described above.

Using the above-described formula, D was obtained. Specifically, the $M_t/m_\infty$ value of the formula was replaced by the B/A value, the particle size (3 mm) was substituted for a, and 2 hours was substituted for t relating to the blowing time. For reference, upon applying the formula above, the values from the case where n is 1 to the case where n is 10 were added up.

In this regard, the TVOC values measured in the equilibrium states of Sample 1 and Sample 2 and the value of the diffusion coefficient (D) obtained according to the formula are as shown in Table 2 below.

TABLE 2

| | TVOC of Sample 1 (ppm) (Reference) | TVOC of Sample 2 (ppm) (after blowing) | Diffusion Coefficient (D) |
|---|---|---|---|
| Temperature (60° C.) | 273.5 ppm | 43.2 ppm | $4.33 \times 10^{-11}$ |

Simulation of Process

The process was simulated based on the calculated diffusion coefficient (D) and equilibrium constant (K). The initial values input in relation to the simulation are as shown in Table 3.

[Initial Value Information]

Diffusion coefficient (D): $4.33 \times 10^{-11}$ at 60° C.

(However, upon changing the temperature, it is calculated by $4.19 \times 10^{-12} \times \exp(-0.03814T)$, where T is a temperature)

Equilibrium constant: 124.1 at 60° C.

(However, upon changing the temperature, it is calculated by $K = 10^{(1181.85/T - 1.51187)}$, where T is a temperature)

Polymer (particle) relation: diameter 3 mm, mass 2 g, specific heat 1500 J/kgK, density 1,070 kg/m$^3$, thermal conductivity 0.22 W/mK Blowing gas: temperature 70° C., flow rate 1,000 kg/hr, specific heat 1000 J/kgK, convection heat transfer coefficient 2 W/m$^2$K Blowing time: 1200 minutes Loading height of polymer in silo: 4.5 m Silo: height 4.5 m, diameter 1.5 m, bulk density 500 kg/m$^3$ Polymer temperature: 50° C.

Number of layers in divided silo: 1,000

TVOC contained in polymer: 275.3 ppm

Specifically, the simulation related to FIG. 4 records how the amount of volatile organic compounds changes in a plurality of silos as the blowing time for the polymer particles (pellets) loaded in the silo increases, where the results of the case in which the pellet temperature is changed (Case 1) and the case in which the flow rate of the hot air is changed (Case 2) are compared and shown on the basis of a reference controlled to have predetermined pellet temperature and blowing (hot air) flow rate. In the graph of FIG. 4(a), the Y-axis values are calculated as the reduced ratios according to the blowing time, relative to the amount of the initial volatile organic compounds, and the X-axis means the blowing time. Based on the dotted line drawn at a height of a value of about 0.1 in the Y-axis, it can be seen that if it is difficult to change the temperature of the pellet particles or the blowing flow rate, at least a blowing time of at least 240 minutes should be secured. On the contrary, it can be seen that if the change of the blowing time, that is, the silo residence time is impossible, the temperature of the pellet particles should be raised or the flow rate of hot air should be increased. Consequently, the method of the present application can be used to determine process conditions such as the blowing time, the blowing flow rate, or the temperature of the pellets required to obtain the desired (residual) amount of volatile organic compounds. FIG. 4(b) is the results of analysis through the absolute amount of TVOC.

FIG. 5 also shows a result of simulating a process of removing volatile organic compounds from a polymer based on empirically obtained diffusion coefficients and equilibrium constants, as described above. In FIG. 5, the diffusion coefficient value and the equilibrium constant value of the reference are the same as those of the reference used in the simulation of FIG. 4. Specifically, in the simulation of FIG. 5(a), the results of the case where the diffusion coefficient was increased twice (Case 3) and the case where the equilibrium constant was increased twice (Case 4) were compared (other blowing conditions were the same). It can be seen through Case 3 that when the diffusion coefficient is increased, the decreasing amount of volatile organic compounds is larger even if the blowing time is the same. In addition, it can be seen through Case 4 that when the equilibrium constant is increased, the equilibrium state is easily reached even if a small amount of volatile organic compounds is discharged into the air, and as a result, the volatile organic compounds are no longer discharged from the particles. These results are in agreement with the meaning of the diffusion coefficient related to the diffusion rate of the volatile organic compounds discharged from the inside of the particles and the meaning of the equilibrium constant concerning the ratio of the amount of the volatile organic compounds possessed by the particles per unit volume to the amount of the volatile organic compounds possessed by the blowing gas per unit volume. In addition, this may mean that the diffusion coefficient and equilibrium constant may be important factors in the removal of volatile organic compounds through blowing. FIG. 5(b) shows the results through the absolute amount.

The invention claimed is:

1. A method for determining process conditions to remove volatile organic compounds from a polymer by blowing a gas, comprising:
calculating a diffusion coefficient (D) and an equilibrium constant (K) of the polymer; and simulating a process of removing the volatile organic compounds based on the calculated diffusion coefficient and equilibrium constant,
wherein the diffusion coefficient (D) and the equilibrium constant (K) are measured or calculated at a plurality of temperatures, respectively.

2. The method according to claim 1, wherein an amount of volatile organic compounds is measured in a headspace of a container storing the polymer, and the diffusion coefficient (D) and the equilibrium constant (K) are calculated from the measured value.

3. The method according to claim 2, wherein the amount of volatile organic compounds is measured in an equilibrium state of a system defined by the sealed container containing the polymer.

4. The method according to claim 2, wherein the amount of volatile organic compounds is measured using gas chromatography.

5. The method according to claim 1, wherein the diffusion coefficient (D) is calculated using the following relation equation 1 and the following formula:

$$M_2 = \frac{B}{A} \cdot M_1 \qquad \text{[Relation Equation 1]}$$

$$\frac{M_t}{M_\infty} = 1 - \frac{6}{\pi^2} \sum_{n=1}^{\infty} \frac{1}{n^2} \exp(-Dn^2\pi^2 t/a^2) \qquad \text{[Formula]}$$

wherein, in the Relation Equation 1 above, A and B are amounts of volatile organic compounds measured in headspaces of different containers, where A is an amount of volatile organic compounds measured in the headspace of the container containing the polymer not subjected to blowing and B is an amount of volatile organic compounds measured in the headspace of the container containing the polymer subjected to blowing, and in the Formula above, t is a time for which the blowing treatment is performed on the blown polymer to measure B, a is a particle size of the polymer, D is the diffusion coefficient, and the value of B/A is equal to the value of $M_t/M_\infty$.

6. The method according to claim 1, wherein the equilibrium constant (K) is calculated using the following relation equation 2:

$$K = \left(\frac{B}{A-B}\right) \cdot \frac{V_g}{V_s} \qquad \text{[Relation Equation 2]}$$

wherein, in the Relation Equation 2 above, A is an amount of volatilized volatile organic compounds measured in the headspace when one sealed container storing the polymer reaches a first equilibrium state, B is an amount of volatilized volatile organic compounds measured in the headspace, when the container is opened for a predetermined time and sealed again after measuring the A and then the container reaches a second equilibrium state, and $V_s$ is a volume of the polymer stored in the container and $V_g$ is the volume of the headspace.

7. The method according to claim 1, wherein it is assumed that the simulating is a simulation of a process that a gas is blown into a silo, in which a polymer is loaded and stored at a predetermined height, for a predetermined time, the silo is equally divided into n layers containing the polymer of the same loading height and the gas flows from the first layer to the n-th layer sequentially.

8. The method according to claim 7, wherein for each of the n-equally divided layers, energy balance and material balance are calculated from the first layer to the n-th layer sequentially.

9. The method according to claim 8, wherein the simulating comprises:
inputting an initial value;
firstly, using an energy balance calculation between a polymer and a blowing gas present in the n-th layer to calculate a changed temperature of the polymer and a changed temperature of the blowing gas;
secondly, calculating an amount of volatile organic compounds discharged from the polymer present in the n-th layer; and
thirdly, calculating an amount of the volatile organic compounds moving from the inside of the polymer present in the n-th layer to the surface of the polymer.

10. The method according to claim 9, wherein the initial value comprises the equilibrium constant (K) and the diffusion coefficient (D).

11. The method according to claim 10, wherein the initial value further comprises one or more selected from the group consisting of a size of a polymer, mass of a polymer, specific heat of a polymer, density of a polymer, a temperature of a blowing gas, a flow rate of a blowing gas, specific heat of a blowing gas, a blowing time of a gas, a loading height of a polymer in a silo, a temperature of a polymer, a number of layers in the divided silo, an amount of volatile organic compounds contained in a polymer and a size of a silo.

12. The method according to claim 9, wherein the calculating the amount of volatile organic compounds discharged from the polymer present in the n-th layer is calculated based on the equilibrium constant (K) and the third step is calculated based on the diffusion coefficient (D).

13. The method according to claim 9, wherein the amount of volatile organic compounds that the polymer present in each layer has on its surface or the change thereof is calculated as the blowing time elapses.

14. The method according to claim 13, further comprising a step of evaluating validity of an input initial value and determining process conditions based on the calculated amount of the volatile organic compounds or the change thereof.

15. A method for determining process conditions to remove volatile organic compounds from a polymer by blowing a gas, comprising:
calculating a diffusion coefficient (D) and an equilibrium constant (K) of the polymer; and simulating a process of removing the volatile organic compounds based on the calculated diffusion coefficient and equilibrium constant,
wherein an amount of volatile organic compounds is measured in a headspace of a container storing the polymer, and the diffusion coefficient (D) and the equilibrium constant (K) are calculated from the measured value.

16. The method according to claim 15, wherein the amount of volatile organic compounds is measured using gas chromatography.

17. The method according to claim 15, wherein the amount of volatile organic compounds is measured in an equilibrium state of a system defined by the sealed container containing the polymer.

18. The method according to claim 15, wherein the diffusion coefficient (D) is calculated using the following relation equation 1 and the following formula:

$$M_2 = \frac{B}{A} \cdot M_1 \qquad \text{[Relation Equation 1]}$$

$$\frac{M_t}{M_\infty} = 1 - \frac{6}{\pi^2} \sum_{n=1}^{\infty} \frac{1}{n^2} \exp(-Dn^2\pi^2 t/a^2) \qquad \text{[Formula]}$$

wherein, in the Relation Equation 1 above, A and B are amounts of volatile organic compounds measured in headspaces of different containers, where A is an amount of volatile organic compounds measured in the headspace of the container containing the polymer not subjected to blowing and B is an amount of volatile organic compounds measured in the headspace of the container containing the polymer subjected to blowing, and in the Formula above, t is a time for which the blowing treatment is performed on the blown polymer to measure B, a is a particle size of the polymer, D is the diffusion coefficient, and the value of B/A is equal to the value of $M_t/M_\infty$.

19. The method according to claim 15, wherein the equilibrium constant (K) is calculated using the following relation equation 2:

$$K = \left(\frac{B}{A-B}\right) \cdot \frac{V_g}{V_s} \qquad \text{[Relation Equation 2]}$$

wherein, in the Relation Equation 2 above, A is an amount of volatilized volatile organic compounds measured in the headspace when one sealed container storing the polymer reaches a first equilibrium state, B is an amount of volatilized volatile organic compounds measured in the headspace, when the container is opened for a predetermined time and sealed again after measuring the A and then the container reaches a second equilibrium state, and $V_s$ is a volume of the polymer stored in the container and $V_g$ is the volume of the headspace.

* * * * *